United States Patent [19]

Claussen

[11] Patent Number: 5,086,404
[45] Date of Patent: Feb. 4, 1992

[54] DEVICE FOR SIMULTANEOUS CONTINUOUS AND SEPARATE RECORDING AND MEASUREMENT OF HEAD AND BODY MOVEMENTS DURING STANDING, WALKING AND STEPPING

[76] Inventor: Claus-Frenz Claussen, Kurhausstrasse 12, D-8730 Bad Kissingen, Fed. Rep. of Germany

[21] Appl. No.: 677,372

[22] Filed: Mar. 27, 1991

Related U.S. Application Data

[63] Continuation of Ser. No. 486,128, Feb. 28, 1990, abandoned.

[51] Int. Cl.⁵ .......................... G06G 7/48; G09G 3/02; G01B 11/26
[52] U.S. Cl. ..................................... 364/559; 356/152; 358/104
[58] Field of Search ............... 364/559, 560, 525, 550, 364/551.01; 356/141, 152; 250/221, 224, 557, 561; 358/105, 107

[56] References Cited

U.S. PATENT DOCUMENTS

| | | | |
|---|---|---|---|
| 4,111,555 | 9/1978 | Ellis | 356/141 |
| 4,146,924 | 3/1979 | Birk et al. | 364/559 X |
| 4,193,689 | 3/1980 | Reymond et al. | 356/152 |
| 4,209,254 | 6/1980 | Reymond et al. | 356/141 X |
| 4,356,387 | 10/1982 | Tsubota et al. | 250/221 X |
| 4,613,942 | 9/1986 | Chen | 250/557 X |
| 4,625,108 | 11/1986 | Nestel et al. | 356/141 X |
| 4,649,504 | 3/1987 | Krouglicof et al. | 364/559 |
| 4,709,580 | 11/1987 | Butts, Jr. et al. | 356/141 X |
| 4,753,569 | 6/1988 | Pryor | 364/559 X |
| 4,807,166 | 2/1989 | Zalenski | 364/571.06 |
| 4,847,485 | 7/1989 | Koelsch | 250/221 |
| 4,896,962 | 1/1990 | Menn et al. | 356/152 |
| 4,928,175 | 5/1990 | Haggrén | 364/559 |
| 4,956,794 | 9/1990 | Zeevi et al. | 356/152 X |
| 4,964,722 | 10/1990 | Schumacher | 356/141 X |

FOREIGN PATENT DOCUMENTS 0152905 8/1985 European Pat. Off. .

*Primary Examiner*—Joseph L. Dixon
*Attorney, Agent, or Firm*—Toren, McGeady & Associates

[57] ABSTRACT

An apparatus and method for the simultaneous, continuous and separate recording and measurement of head and body movements during standing and walking, including various optical markers mounted upon the head and the trunk of a test person, and a device for continuously receiving and recording optical signals from the markers, which device is stationarily fixed at a distance from the test person. The device being easy to handle, allows a time critical spectral analysis of the movement patterns, avoids overlapping of light tracings during recording of the optical signals, distortions of the measurements due to parallaxes when observing the body at various locations and central scotoma or an area of loss of visibility of the optical markers underneath of the device. At least three photoelectric cells being permanently mounted and fixed in a polygonal relation, and the device successively compares and levels quantitatively the values if the measurements of the photoelectric cells, which are permanently called and transmitted to a central data processing unit by a flow of data. Thus, the device installs a cylindrical vertical projection upon the standing or moving person being recorded.

15 Claims, 7 Drawing Sheets

DEVICE FOR SIMULTANEOUS CONTINUOUS AND SEPARATE RECORDING AND MEASUREMENT OF HEAD AND BODY MOVEMENTS DURING STANDING, WALKING AND STEPPING

This is a continuation application of Ser. No. 07/486,128, filed Feb. 28, 1990, now abandoned.

BACKGROUND OF THE INVENTION

1. FIELD OF THE INVENTION

The present invention relates to a method and apparatus for determination of a simultaneous, permanent and separate recording and measurement of the head and trunk movements of a body in one plane during standing and walking. The invention includes optical markers, which are mounted upon the head and the trunk of the test person. Such an apparatus also includes a device which is stationarily put in operation at a distance above the test person, and continuously receives and records the optical signals of the markers.

2. DESCRIPTION OF THE PRIOR ART

A similar device has been used until now by means of the so-called cranio-corpo-graphy (CCG), which has been described in the literature:

"Ein einfacher, objektiver und quantitativer Gleichgewichstest für die Praxis Forschungsbericht Cranio-CorpoGraphy (CCG), Schritfenreihe des Hauptverbandes der gewerblichen Berufsgenossenschaften eV, Lindenstrasse 78, D 5205 St. Augustin 2, West Germany, Juni 1986."

However, several disadvantages are adhered to this well-known instrument. For obtaining a sufficient distance between the test person and the optical receiver and recorder, a mirror is attached to the ceiling into which a camera is centrally directed from below. Thus, an area of loss is visibly of the optical marker is created centrally underneath the camera, within which the markers cannot be observed. Another disadvantage lies in the fact that handling the camera involves difficult overhead maneuvering. Since all the exposures can only be recorded outside of the central scotoma, distortions of the measurements occur due to parallaxes, with an increasing impact when moving towards the border of the field of observation. Since the photographic recording is two dimensional, a time critical spectral analysis of the movement patterns cannot be achieved, even though it is diagnostically important, due to the hierarchically organized central nervous movement regulation, including the brain hemispheres, brain stem and spinal cord. Finally, an analysis of the movement patterns of the various marker points upon the head and the body is impaired and partly impossible due to overlapping of the light tracings during the swaying movements of the head and body, when standing stepping or walking.

Another prior art device is described in U.S. Pat. No. 4,375,674, issued Mar. 3, 1983, for "Kinesiometric Method and Apparatus" to William E. Thawnton. Disclosed therein are an apparatus and method for the determination of functional capability of bodies. Reach, as well as velocity, acceleration and force generation at various positions, may be determined for parts of the body by a three-dimensional kinesimeter, equipped with an ergometer. This invention finds particular application to the measurement of human task performing capabilities. A three camera video position detector system is positioned equidistant around a stationary reference lamp. The test subject, whose anthropometric characteristics are to be observed, is regularly positioned within the field of view of the camera system. The test person is kept in fixed relation to the reference site by body belts, as shown in FIGS. 5 and 10 thereof. The recorder light fixed to a part of the body, for instance an arm or a hand, is then recorded through cameras when moving. The system needs a complicated calibration procedure to be appropriately programmed with proper scale factors and locations, as well as zero references used in calculations of position for accurate dimensional measurements, in which one of the lamps serves as a reference lamp. This invention does not allow recording of locomotor tracings over the plain field of visibility, as the body must be kept close to the reference lamp. It is therefore used for establishing maximum reach envelopes. A simultaneous recording of several head and body marker points during walking consequently cannot be achieved since always only the coordinates of one marker point are put into relation with the central coordinates of the reference lamp. Also, the ergometer needs to keep the body stationary, as depicted in the figures.

A further variety of techniques, which have been developed to attempt to measure one aspect or another of human activities, have also been described and discussed in the background of the invention section of U.S. Pat. No. 4,375,674.

SUMMARY OF THE INVENTION

It is an object of the present invention to provide a method and apparatus for recording head and body movements during standing and walking, as described above, which avoids overlapping of the light tracings during recording and distortions of the measurements due to parallaxes, when observing the body at various locations, and avoids central scotoma or an area of loss of visibility of the optical markers underneath the recording device. The present invention achieves this objective with a device having at least three photoelectrical cells which are stationarily fixed in a polygonal shape above the test person or object. The values of measurements of different intensities at the different photoelectric cells are regularly successively compared with each other, and are input into a central data processing unit by a flow data.

By means of the polygonal arrangement of the photoelectric cells, the present invention avoids a central area of loss of visibility of the optical markers underneath the device, and all the optical distortions of the measurements at varying positions of the test person, since the object viewed is inside of a cylinder of the "electronic objective". The invention also includes that the values of measurement of the photoelectric cells of different light intensities are regularly successively compared with each other, and they are permanently input into a central data processing unit by means of a series of data. The comparison of the measurements rotates successively and regularly between all the photoelectric cells and several generations of virtual values. Thus, a temporal and spatial structure of the movement patterns of the various head and body marker points is achieved. The resulting data series and curves additionally allow a spectral analysis of the movements of the head and body points being marked. Thus, whose body movements as well as the movements of parts of the body and the differences between the movements of various parts of the body, for instance, between head and trunk, can be calculated and graphed. All these calculations can be executed simultaneously upon all the body points recorded. The differences in the movement patterns of various parts of the human body, which are important for medical diagnostics, can be displayed in digital time series of the measurements, as well as by means of graphical curves for each of the points being recorded, as well as by statistical plots.

A preferred polygonal arrangement of the photoelectric cells, with respect to this invention, is a hexagon. The hexagon of photoelectrical cells delivers a sufficient amount of data for a precision measurement. Additionally, the hexagon makes it possible to closely attach several polygons of photoelectric cells in a honeycombed manner for surveying the complete surface of an entire room. Such a complete viewing of a whole room without any optical distortions in the plane of observations cannot be achieved with the procedures known prior to the present invention and cited above.

According to a further embodiment of the invention, the central data processing unit is a digital computer. This computer compares and calculates the bit coded measurements of light differences between the photoelectric cells in a successively rotating manner on real and virtual point comparisons. Thus, the points of maximal marker lights are determined in the plane. Additionally, the computer calculates the synthesis of the light tracings in the plane, the spectral analysis of the marker movements with respect to frequency and amplitude etc., as well as the numerical and graphical display of the parameters and the curves. Important clinical and diagnostic parameters are also evaluated numerically and graphically, like longitudinal displacement, longitudinal sway, lateral sway, angular deviation, whole body spin, angular distortion of the head with respect to the trunk, differences in the sways between head and trunk, and configurations of preferential zones of movements.

In case of preferred high precision marker localization, it is necessary to evaluate a maximum of possible light intensity comparisons. Therefore, the invention also includes a light source at the very center of the polygon of photoelectric cells, controlled by the central processing unit, which permits regulation of the intensity and the color of the light during continuous light emission, and during intermittent light emission the intensity, color and rhythm of the light. The markers, being reflectors in this case, can be received separately with short time intervals from calculation to calculation. Thus, one marker is only visible at each short observation interval.

For the same purpose, in another embodiment of the invention, the central data processing unit is connected with the photoelectric cells through a remote control so that the photoelectric cells can be modulated with respect to their photoelectric sensitivity and/or with respect to their sensitivity in combination with adaptive or controlled modulation of the central light emitting system.

In a further embodiment of the invention, the photoelectric cells are constructed with a dual output mode, which can be selected for output of analogous signals or output of signals which are directly analogue to digital reconverted. The latter alternative implies the advantage that the central processing unit is continuously provided with signals, which can be calculated immediately. This excludes the susceptibility to faults, for example, due to untoward resistances in the wires, magnetic fields, etc.

It is also advantageous to provide the digital computer with at least one interface for the photoelectric cells with a multiplexer function, as well as with an interface for an analogue to digital converter. Of course, each of the photocells can have its own input into the central processing unit.

The detailed description of the invention is given in connection with device for medical investigation of head and body instability during standing and stepping.

DETAILED DESCRIPTION OF THE PREFERRED EMBODIMENTS

Figure 1:
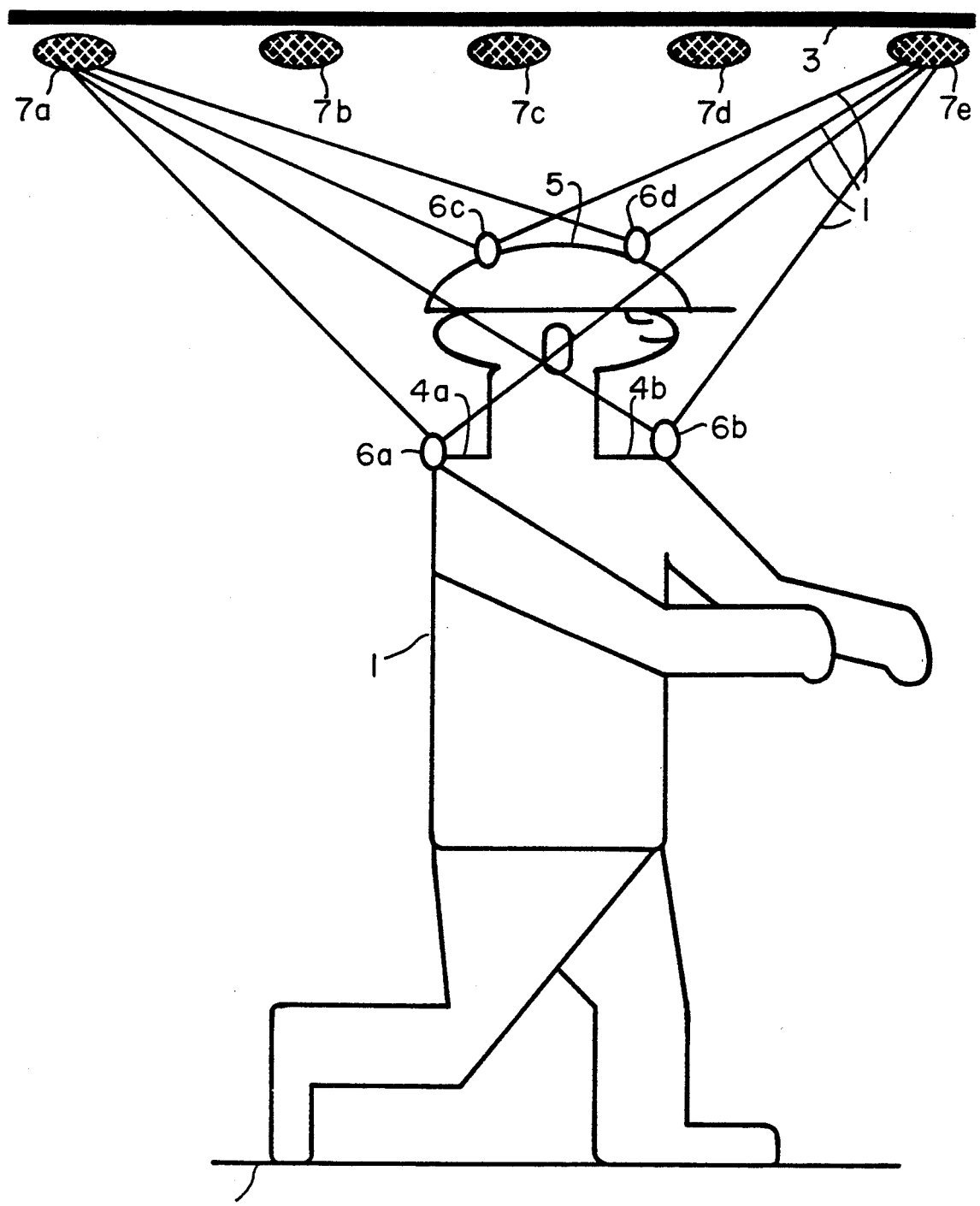
FIG. 1 is a lateral view of a device pursuant to the present invention, mounted in a room.

FIG. 1 shows a test person 1, who is moving in a room, of which the floor 2 and the ceiling 3 are visible. Markers 6a–6d are attached on the shoulders 4a, 4b of the test person, and on a helmet 5 on the test person's head. The markers 6a–6a emit light beams 1. These light beams 1 are received and processed by photoelectric cells 7a–7h, which are attached in fixed positions to the ceiling 3.

Figure 2:
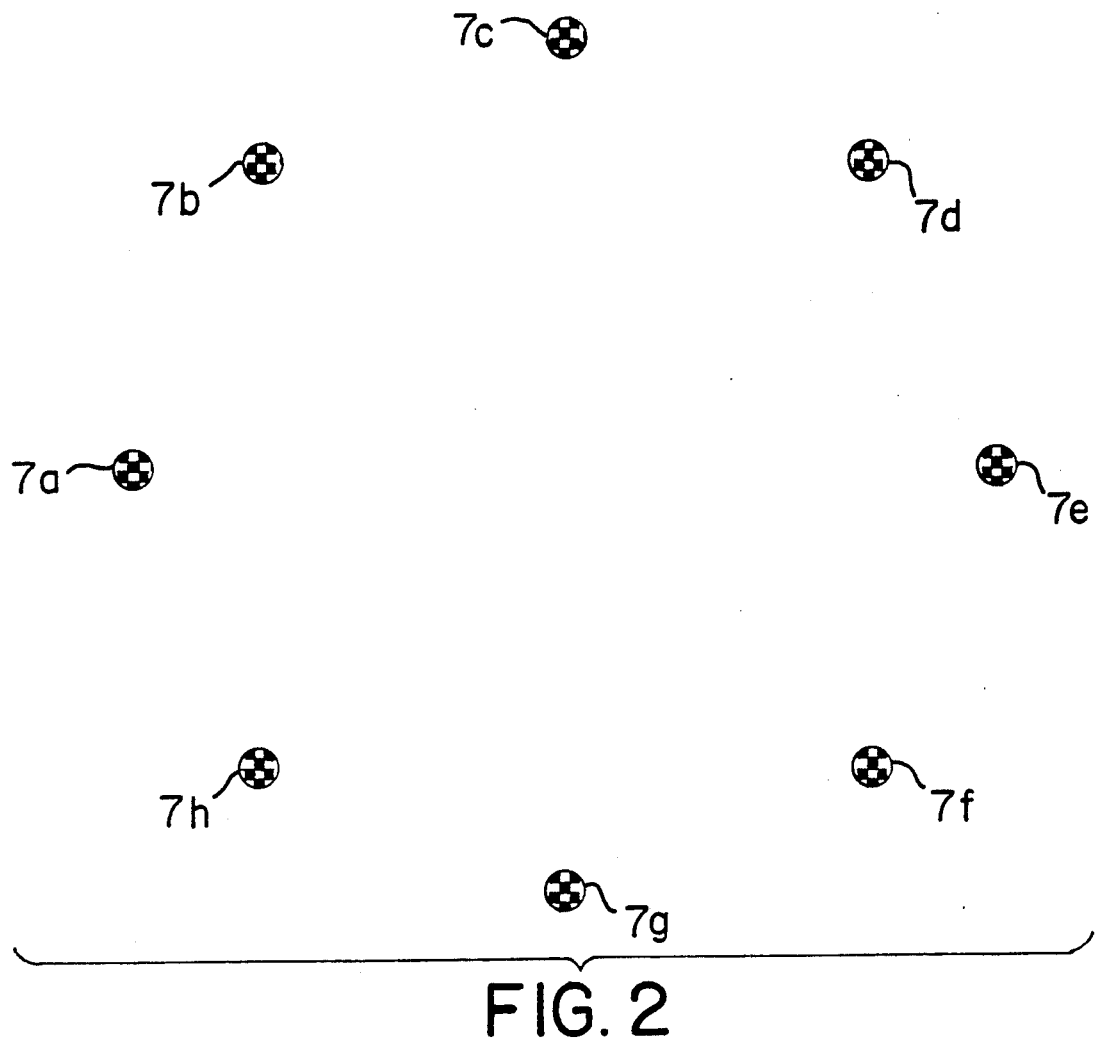
FIG. 2 shows the position of the photoelectric cells according to FIG. 1 in an upward view.
Figure 3:
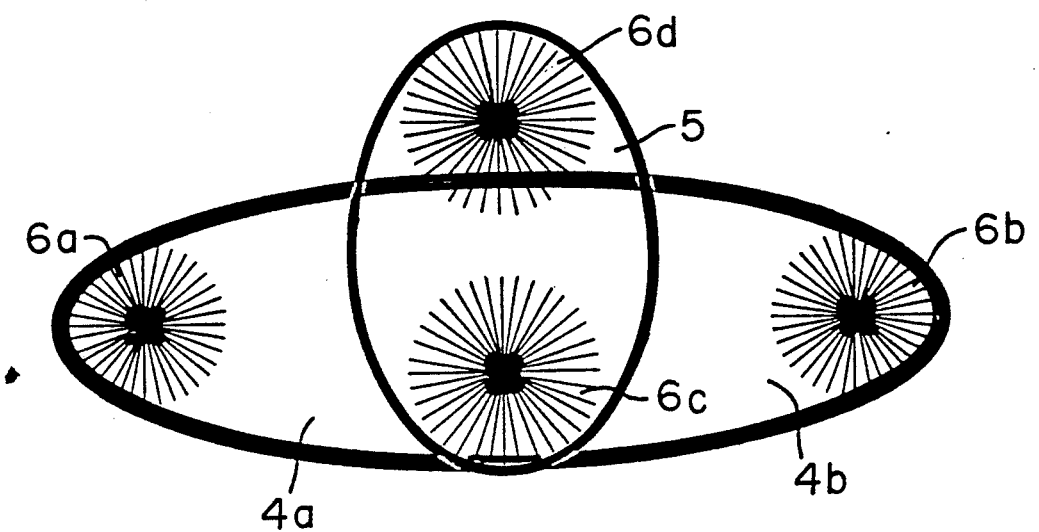
FIG. 3 is a downward view upon the test person according to FIG. 1.

As shown in FIG. 2, the photoelectric cells 7a–7h are arranged in the shape of a regular octagon. FIG. 3 demonstrates the position of the markers 6a–6d on the shoulders 4a, 4b and the helmet 5.

Figure 4:
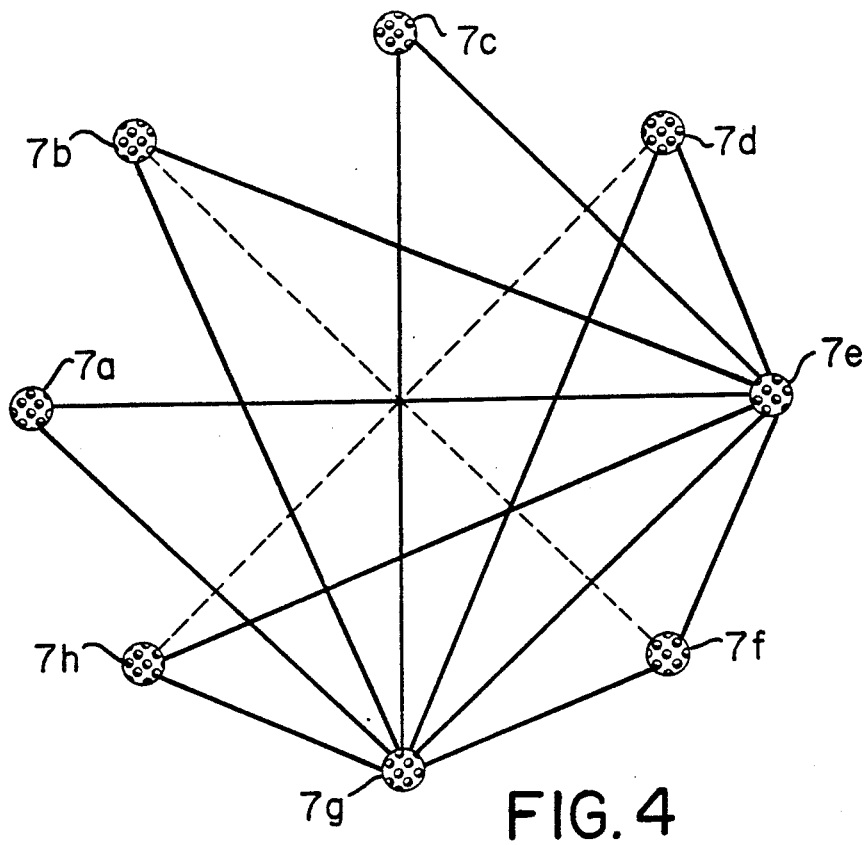
FIG. 4 is a schematic display of a part of the rotating paired calculation and leveling of the light intensities of the photoelectric cells fixed in polygonal position.
Figure 5:
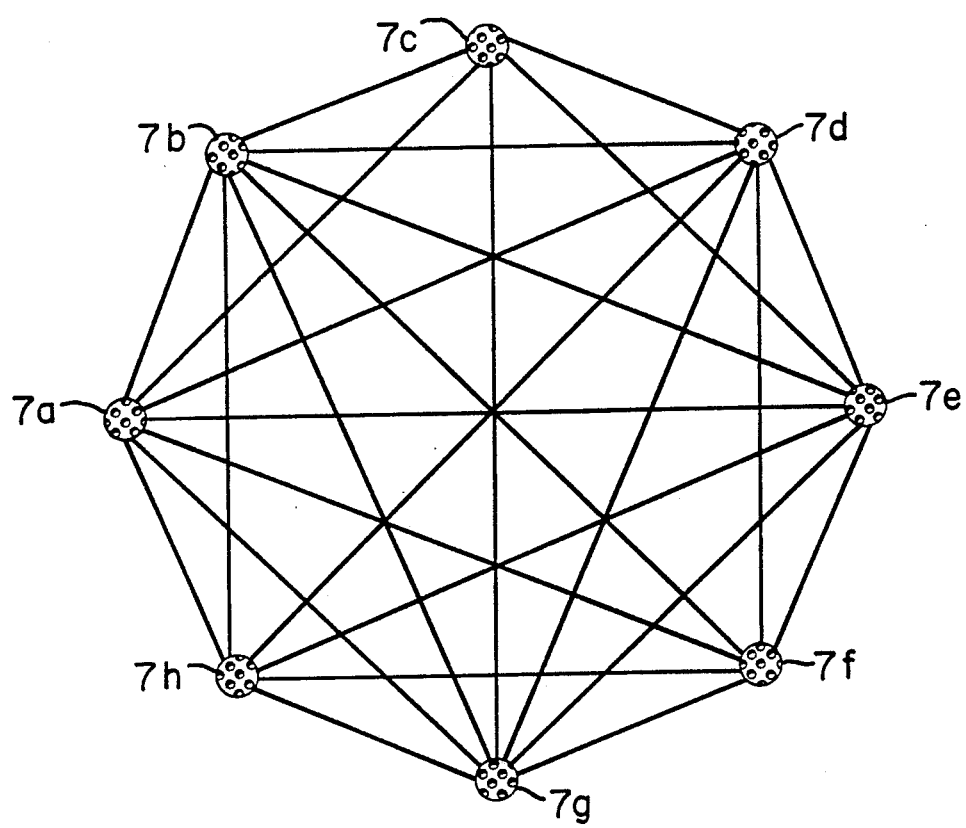
FIG. 5 is a schematic illustration of a complete direct rotating paired calculation and leveling of the light intensities of the photoelectric cells.

FIG. 4 schematically illustrates part of the rotating pair calculation and leveling of the light intensities of the photoelectric cells 7a–7h, while FIG. 5 illustrates the complete calculation and leveling of light intensities.

Figure 6:
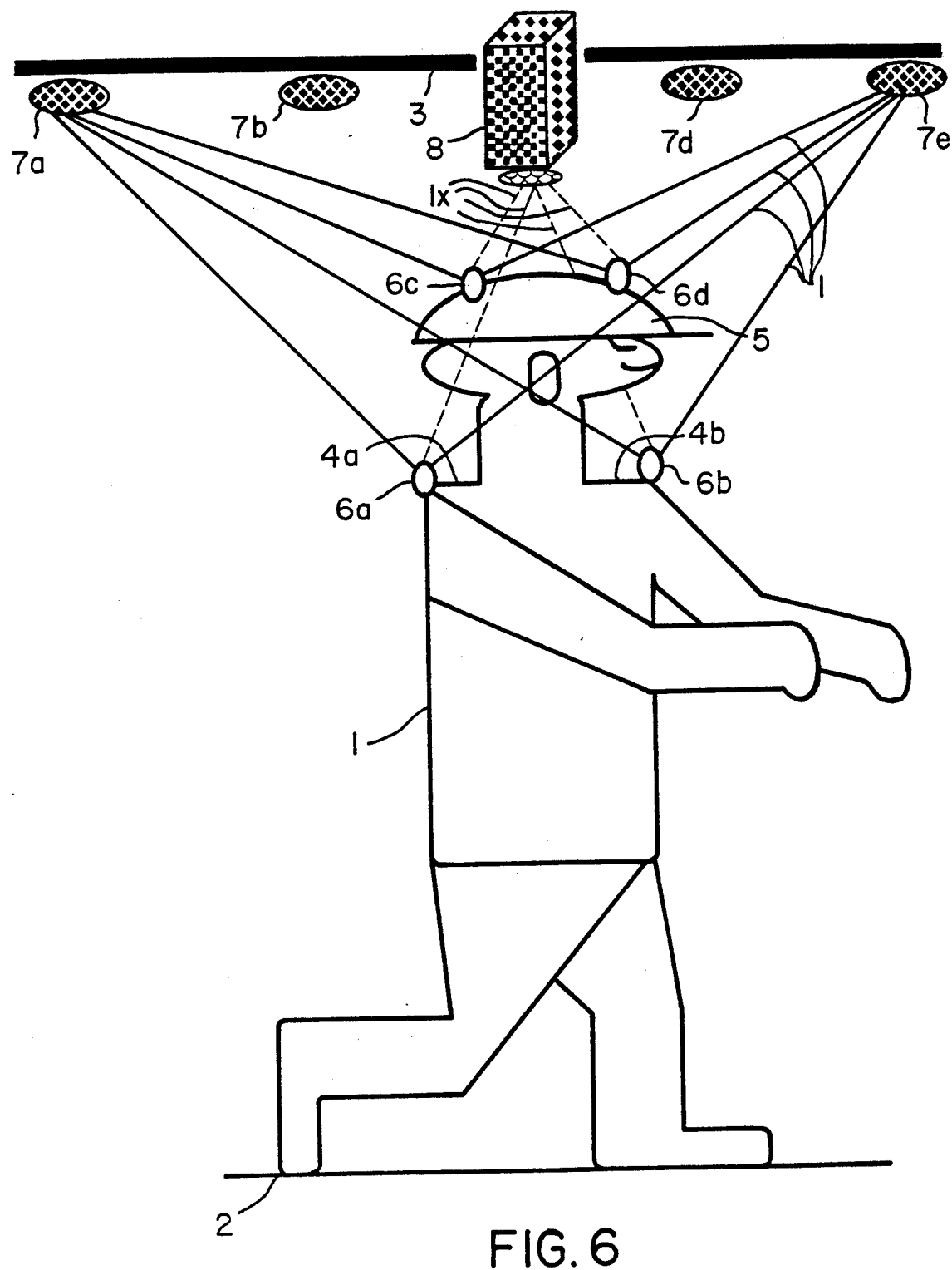
FIG. 6 is a lateral view of a modified embodiment of the invention with a light emitting system through reflector markers.

FIG. 6 basically illustrates the same arrangement as FIG. 1, with one difference. The difference being a light source 8 installed in the very center of the polygon of the photoelectric cells 7 for the stimulation of the passive, only reflecting markers 6a–6d, which then do not have their own light sources. The light beams being released from the central light source 8, which are received by the markers 6a–6d, are denoted with $1_x$.

Figure 7:
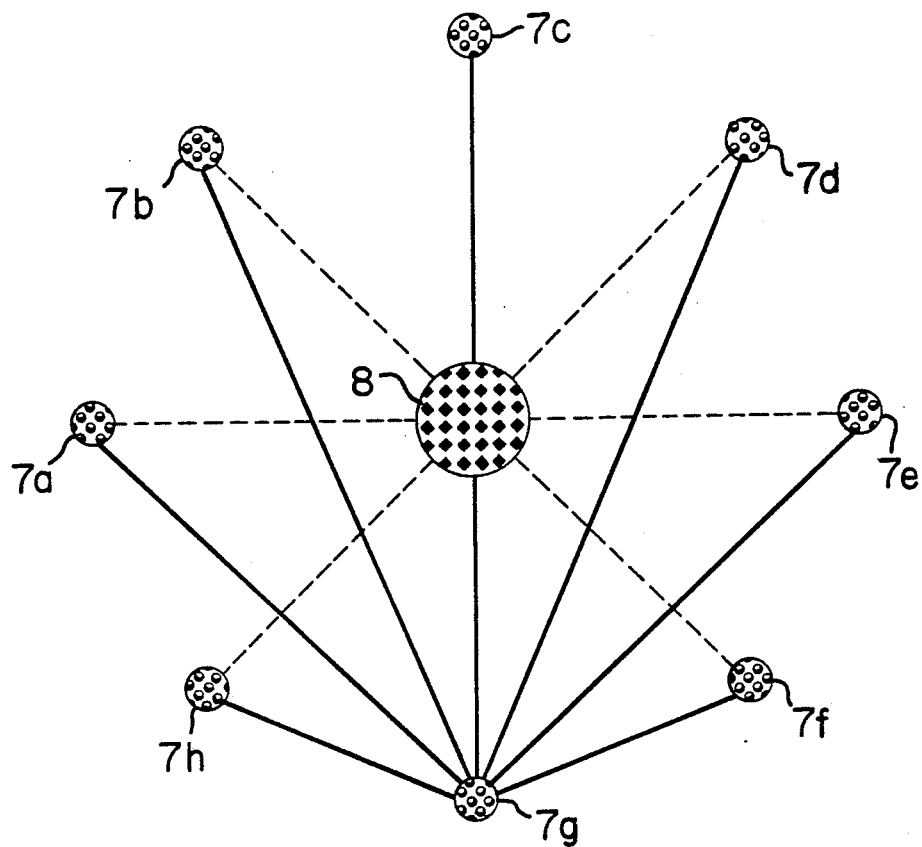
FIG. 7 is a layout of the position of the photoelectric cells according to FIG. 6 and the schematic demonstration of partial rotating calculation and leveling of the light intensities of the photoelectric cells.

The position of the photoelectric cells 7a–7h of FIG. 6 are schematically shown in FIG. 7, which demonstrates a partial rotating paired calculation and leveling of light intensities.

Figure 8:
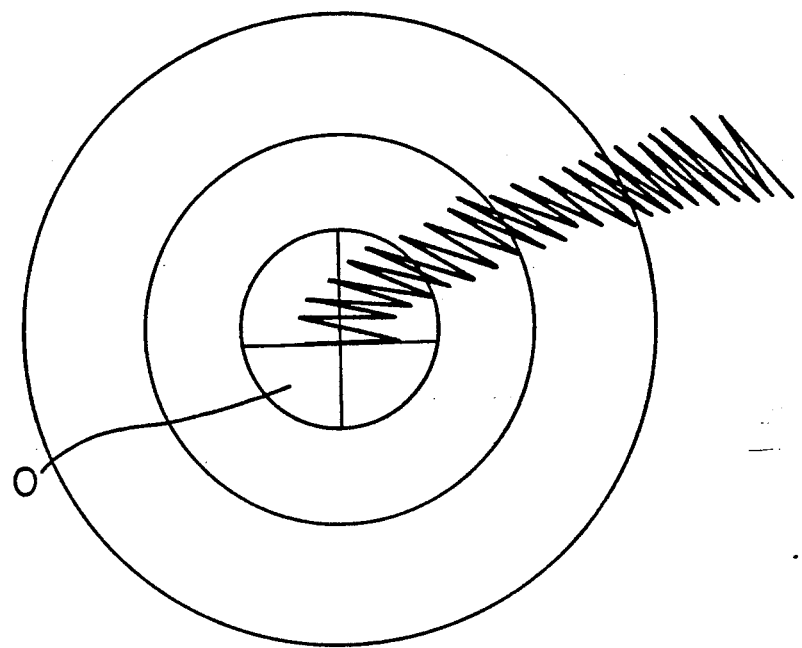
FIG. 8 is a measured light tracing of the movements of a randomly chosen marker point.

FIG. 8 demonstrates a body movement pattern, like a cut line of a scythe of a test person 1, stepping on a spot, beginning at a starting point 0 and moving anteriorly, even though he believes that he is stepping on the spot. The movement pattern is taken from a calculated tracing of any randomly selected marker 6.

Figure 9:
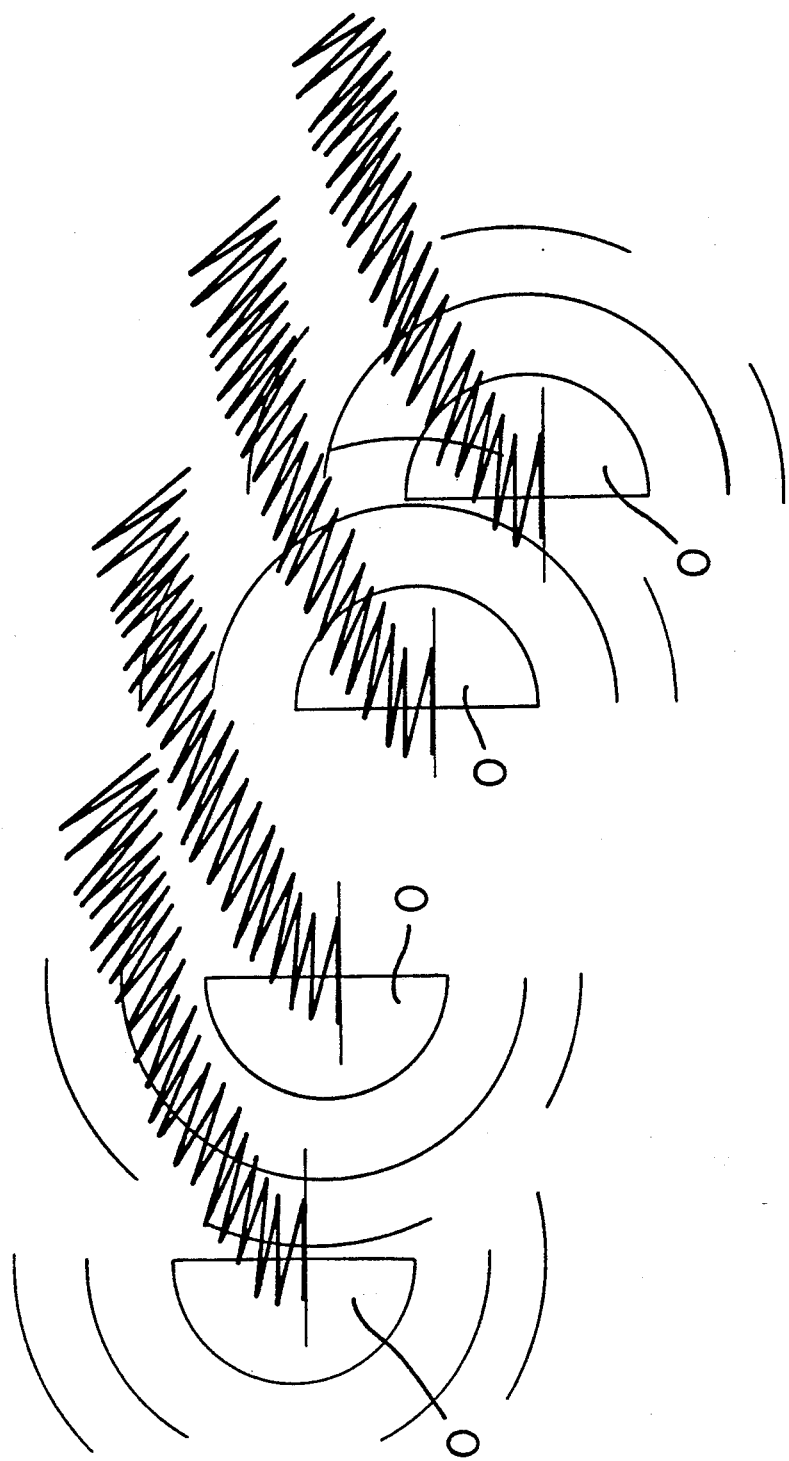
FIG. 9 shows light tracings of the movement patterns of all four marker points.
Figure 10:
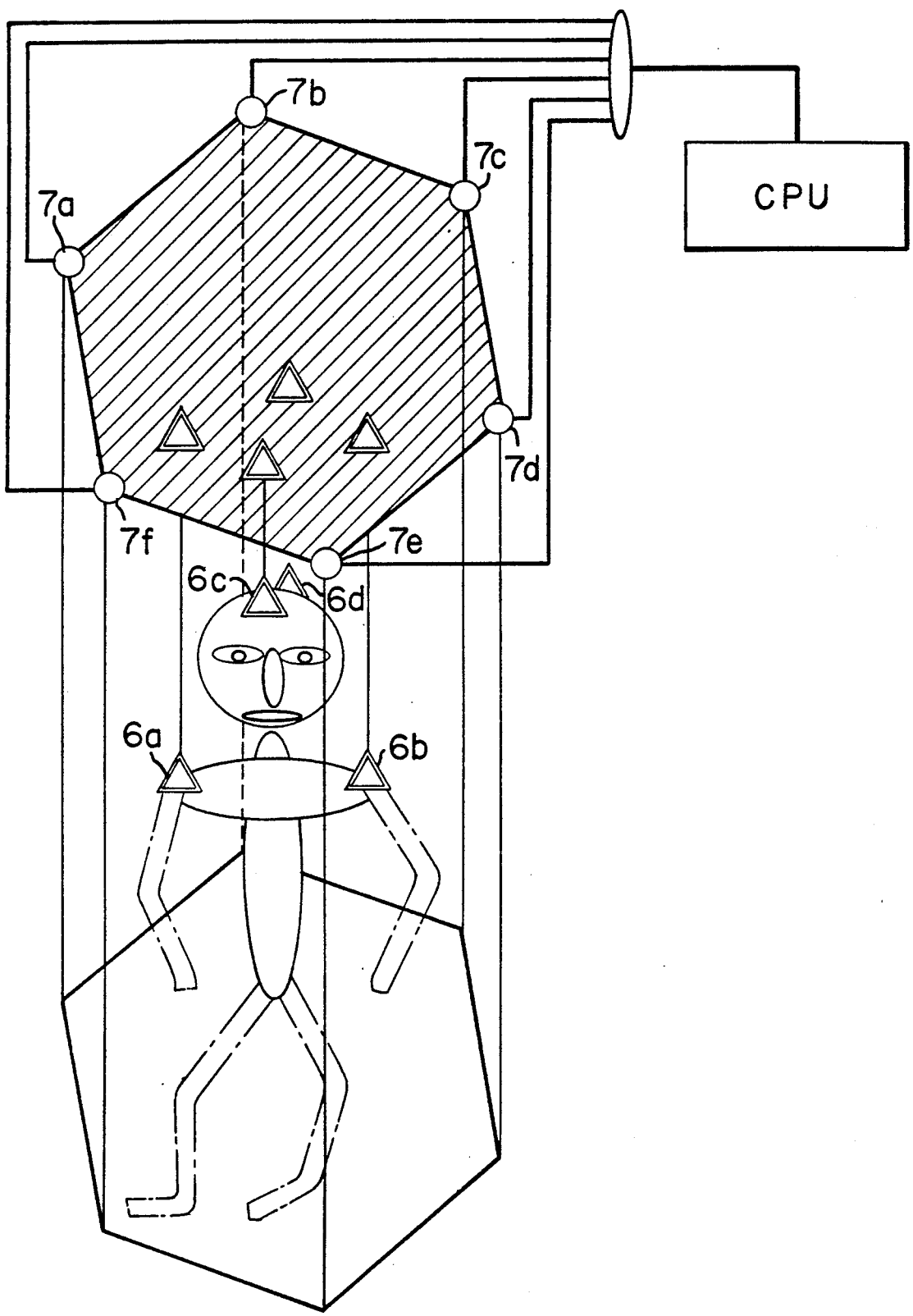
FIG. 10 is an overall view of the inventive apparatus.

FIG. 9 demonstrates the said procedure as in FIG. 8, however, for all 4 markers 6a-6d. Due to separation of the single tracings of the movements by computer processing, each of the tracings can be completely inspected without any loss of visibility or overlap and/or crossing.

The invention has been demonstrated above by means of a medical application. However, other applications are also considered, for instance, the supervision of the movements of personnel in dangerous and hazardous working areas, like, for instance, in nuclear power plants. Besides, the invention may also be applied in conveying systems of exactly localizing and managing movable machineries, tools or parts, as well as for an assembly technique.

The foregoing disclosure and description of the invention is illustrative and explanatory thereof, and various changes in the method steps, as well as in the details of the illustrated apparatus, may be made within the scope of the appended claims without departing from the spirit of the invention.

I claim:

1. An apparatus for continuous and separate recording and measuring of head and trunk movement of a test person, comprising:
    optical markers attached to the head and trunk of the test person, which markers output optical signals;
    means for continuously receiving and recording the optical signals from the optical markers, said receiving and recording means being stationarily fixed above the test person, said receiving and recording means including at least three photoelectric cells arranged in a polygon so as to project a cylindrical vertical projection upon the test person, and so as to measure light intensity of the optical signals and output corresponding signals; and
    central processing means for successively comparing and computing different light intensities of the photoelectric cells against each other for generating virtual data points, measurements from the cells being successively called into the central processing means by a data flow, and thereafter, if necessary for resolution, followed by at least one successive generation of virtual data joints from the light intensity comparisons previously computed, which again are successively and pairwise compared and computed with respect to the virtual data points having coordinates inside the polygon, until the points are projected and displayed with a set precision into a data bank from which the points are transferable into a projection frame.

2. An apparatus as defined in claim 1, wherein said receiving and recording means includes six photoelectric cells arranged in a hexagon.

3. An apparatus as defined in claim 1, wherein said central processing means includes a digital computer.

4. An apparatus as defined in claim 3, and further comprising a light source arranged at the center of the polygon formed by said photoelectric cells, said digital computer being connected to said light source, and said light source being remotely controlled by said central processing means with respect to light intensity and light color of a continuous light emission, as well as light intensity, color and rhythm of an intermittent light emission.

5. An apparatus as defined in claim 4, wherein said photoelectric cells are connected with said digital computer so that said photoelectric cells are modulated according to optimal optical noise/signal ratios balanced with said light source.

6. An apparatus as defined in claim 3, wherein said digital computer includes at least one interface for said photoelectric cells with a multiplexer, as well as an interface for an analog-to-digital converter.

7. An apparatus as defined in claim 1, and further comprising means for switching said photoelectric cells into a mode so that only analog signals are delivered.

8. An apparatus as defined in claim 1, and further comprising means for controlling said photoelectric cells so that said cells deliver signals which are converted from analog to digital.

9. An apparatus as defined in claim 1, wherein the central processing means is responsive to an instruction which limits the number of generations of virtual points being computed so that resolution and precision of the recording and measuring of head and trunk movements is settable.

10. An apparatus for continuous and separate recording and measurement of movements of a test object, comprising:
    optical markers attached to the test object, which markers output optical signals;
    means for continuously receiving and recording the optical signals from the optical markers, said receiving and recording means being stationarily fixed above the test object, said receiving and recording means including at least three photoelectric cells arranged in a polygon so that to project a cylindrical vertical projection upon the test object, and so as to measure light intensity of the optical signals and put out corresponding signals; and
    central processing means for successively comparing and computing different light intensities of the photoelectric cells against each other for generating virtual data points, measurements from the cells being successively called into the central processing means by a data flow, and thereafter, if necessary for resolution, followed by at least one successive generation of virtual data points from the light intensity comparisons previously computed, which again are successively and pair wise compared and computed with respect to the virtual data points having coordinates inside the polygon, until the points are projected and displayed with a set precision into a data bank from which the points are transferably into a projection frame.

11. An apparatus as defined in claim 10, wherein the receiving and recording means includes a plurality of polygons of photoelectric cells in a honeycomb-like arrangement.

12. An apparatus as defined in claim 10, wherein the test object is machinery whose movements are measured and recorded for localizing and managing the machinery.

13. An apparatus as defined in claim 10, wherein the test object is a conveying system for assembly, so as to optimize assembly along the conveying system.

14. A method for continuously, separately and repeatedly recording and measuring movements of a test object by establishing individual tracings of various marker points, comprising the steps of:

attaching optical markers to the test object, which markers output optical signals;

continuously receiving and recording the optical signals from the optical markers, from a fixed position above the test object, said receiving and recording step including measuring light intensity of the optical signals by way of at least three photoelectric cells arranged in a polygon so as to project a cylindrical vertical projection upon the test object, and putting out corresponding signals;

successively comparing and computing different intensities of the photoelectric cells against each other for generating virtual data points, and calling measurements from the cells into the central processing means by a data flow, and thereafter, if necessary for resolution, followed by at least one successive generation of virtual data points from the light intensity comparisons previously computed, which again are successively and pairwise compared and computed, with respect to the virtual data points having coordinates inside the polygon, until the points are projected and displayed with a set precision into a data bank from which the points are transferable into a projection frame; and mounting the tracings of the movement through a computer program in a framewise manner for graphical and numerical evaluation.

15. A method according to claim 14, and further comprising the step of setting resolution and precision of the recording and measuring of movements of the test object by limiting the number of generations of virtual points being computed.

* * * * *